US007813882B2

(12) United States Patent
Some et al.

(10) Patent No.: US 7,813,882 B2
(45) Date of Patent: Oct. 12, 2010

(54) METHOD FOR DETERMINING AVERAGE PROPERTIES OF MOLECULES IN SOLUTION

(75) Inventors: Daniel I. Some, Santa Barbara, CA (US); Steven P. Trainoff, Goleta, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 281 days.

(21) Appl. No.: 12/072,986

(22) Filed: Feb. 29, 2008

(65) Prior Publication Data

US 2009/0222219 A1 Sep. 3, 2009

(51) Int. Cl.
*G01N 31/00* (2006.01)

(52) U.S. Cl. .............................. 702/25; 702/27; 702/28; 422/63; 422/70; 422/100; 210/635; 210/656

(58) Field of Classification Search ................... 702/25, 702/27, 28; 422/63, 70, 100; 210/635, 656
See application file for complete search history.

(56) References Cited

U.S. PATENT DOCUMENTS

| 3,683,678 | A | * | 8/1972 | Yau | ............................. 73/64.54 |
| 6,411,383 | B1 | | 6/2002 | Wyatt | |
| 6,651,009 | B1 | | 11/2003 | Trainoff | |
| 2002/0196446 | A1 | * | 12/2002 | Roth et al. | ................... 356/479 |
| 2004/0043445 | A1 | * | 3/2004 | Daniels | ........................ 435/41 |

OTHER PUBLICATIONS

Keir et al., 'Rayleigh depolarization ratios and molecular polarizability anisotropies of BX3 (X=F, Cl, Br, I). Comparison of Experimental results and ab initio calculations', Jul. 3, 1998, Chemical Physics Letter Publication, pp. 409-414.*

Zimm, Bruno H., The Scattering of Light and the Radial Distribution Function of High Polymer Solutions, J. Chemical Physics, 1948, pp. 1093-1099, vol. 16, No. 12, USA.

Bryce, W. A. J., Multiple and Curvilinear Regression Analysis of Light Scattering Data, Polymer, 1969, pp. 804-809, vol. 10, London.

Debye, P., Molecular-weight Determination by Light Scattering, J. Physical Colloid Chemistry, 1947, pp. 18-32, vol. 51.

Wyatt, P. J., Light scattering and the solution properties of macromolecules, Handbook of Size Exclusion Chromatography, 2004, pp. 623-655, Marcel Dekker, New York.

Mijnlieff,P. F., and D. J. Coumou, Extrapolation of Light-Scattering Data to Zero Scattering Angle, J. Colloid Interface Sci., 1968, pp. 552, vol. 27, Elsevier, USA.

Wyatt Technology Corporation, Dawn Heleos II promotional literature, 2007, Wyatt Technology Corporation, Goleta, USA.

* cited by examiner

*Primary Examiner*—Mohamed Charioui
*Assistant Examiner*—Elias Desta
(74) *Attorney, Agent, or Firm*—Philip J. Wyatt; David N. Villalpando (57) ABSTRACT

A new method is presented for measuring the molecular properties of an unfractionated solution of macromolecules. Sample aliquots spanning a range of concentrations are injected sequentially into a stream of solution and flow towards the detectors. Each aliquot produces, thereby, an effective "peak" whose elements correspond to different concentrations of the diluted aliquot. The weight averaged molar mass, the mean square radius, and the second virial coefficient of the macromolecules in solution are derived from an analysis of the angular and concentration dependence of the scattering signals throughout the corresponding peaks. In contrast to earlier on-line methods, better accuracy is achieved, while using a smaller quantity of sample. A similar method for determining cross virial coefficients between two distinct species of macromolecules is also presented.

40 Claims, 6 Drawing Sheets

Prior Art

Figure 1

Prior Art

Figure 2

Prior Art

Figure 3

Prior Art

METHOD FOR DETERMINING AVERAGE PROPERTIES OF MOLECULES IN SOLUTION

BACKGROUND

Molecules in solution are generally characterized by their weight averaged molar mass M, their mean square radius $\langle r_g^2 \rangle = \int r^2 dm / \int dm$ (here r is the distance from the center of mass of the molecule and dm the mass of a small volume at that distance), and the second virial coefficient $A_2$. In some cases, the third virial coefficient $A_3$ is also of interest. In other cases, the cross-virial coefficient $A_2^{AB}$ between two distinct molecules A and B is of interest. M and $\langle r_g^2 \rangle$ are properties of the individual molecules, averaged over all the molecules in the solution; the virial coefficients are a measure of the average interaction between the molecules as mediated by the solvent. For unfractionated solutions, these properties may be determined by measuring the manner by which they scatter light using the method described by Bruno Zimm in his seminal 1948 paper which appeared in the Journal of Chemical Physics, volume 16 pages 1093 through 1099. The light scattered from a small volume of the solution is measured over a range of angles and concentrations. The collection of light scattering data over a range of scattering angles is referred to more commonly as multiangle light scattering, MALS. The properties derived from the light scattering measurements for a single type of molecule are related through the formula developed by Zimm and corrected by W. A. J. Bryce in *Polymer* 10 804-809 (1969):

$$R^*(c,\theta) = McP(\theta) - 2A_2[MP(\theta)c]^2 - [3A_3Q(\theta) - 4A_2^2 MP^2(\theta)][MP(\theta)]^2 c^3 \quad (1)$$

where $R^*(c,\theta) = R(c,\theta)/K^*$, $R(c,\theta)$ is the measured excess Rayleigh ratio in the direction $\theta$ per unit solid angle defined as $R(\theta) = [I_s(\theta) - I_{solv}(\theta)]r^2/[I_0 V]$, $I_s(\theta)$ is the intensity of light scattered by the solution a function of angle, $I_{solv}(\theta)$ is the intensity of light scattered from the solvent as a function of angle, $I_0$ is the incident intensity, r is the distance from the scattering volume to the detector, V is the illuminated volume seen by the detectors, $K = 4\pi^2 n_0^2/(N_A \lambda_0^4)$, and $K^* = K(dn/dc)^2$, $N_A$ is Avogadro's number, dn/dc is the refractive index increment, $n_0$ is the solvent refractive index, and $\lambda_0$ is the wavelength of the incident light in vacuum. $P(\theta)$ is the form factor of the scattering molecules defined as $P(\theta) = \lim_{c \to 0} R(\theta)/R(0)$. The general form of $P(\theta)$ was derived by P. Debye in J. Phys. Colloid Chem., 51 18 (1947) as:

$$P(\theta) = 1 - P_1 \sin^2\left(\frac{\theta}{2}\right) + P_2 \sin^4\left(\frac{\theta}{2}\right) + \ldots \quad (2)$$

$P_1$ is related to the mean square radius via $$P_1 = \frac{(2k)^2}{3} \langle r_g^2 \rangle,$$

and $k = 2\pi/\lambda$ with $\lambda$ being the wavelength of the incident light in the solvent. $P_2$ is related to the mean square radius $\langle r_g^2 \rangle$ and the mean quadri-radius $\langle r_g^4 \rangle$ via $$P_2 = \frac{2k^4}{45}\left(10\langle r_g^2 \rangle^2 - 3\langle r_g^4 \rangle\right).$$

This equation is an approximation based on a series expansion in powers of concentration and $\sin^2(\theta/2)$; as such, the degree of accuracy depends on the relative magnitudes of the higher order terms.

The standard method, also known as the "plateau method," of carrying out this measurement involves preparing a series of samples with increasing concentrations of known values; sequentially introducing the samples to a MALS detector, whether by inserting glass vials containing the samples in the light beam or by injecting the samples into a flow cell located in the beam; acquiring the scattered intensity at each angle by means of a photodetector; calculating the excess Rayleigh ratios for each concentration and angle; and fitting the data to Eq. (1) to extract M, $\langle r_g^2 \rangle$, $A_2$ and $A_3$.

In the case of injecting the sample into a flow cell containing some previous sample or solution, sufficient volume must be injected in order to "saturate" the cell, i.e. to bring the concentration in the cell to the original, known sample concentration; this may be accomplished by observing the scattering signal and flowing the sample until the value of the signal vs. time reaches a plateau, which occurs asymptotically with an exponential dependence. Alternatively, a concentration detector with a flow cell may be added to the flow path, and sufficient sample must be injected in order for both the MALS and concentration signals attain a plateau over time; in this manner the concentration in the MALS detector may be inferred from the concentration in the concentration detector, to provide the values of R and c in Eq. (1). Typical volumes per injection required to saturate the flow cells are 1-3 mL.

Recognizing the asymptotic approach to the correct concentration values in each cell, a more precise measurement may be obtained by following an increasing concentration series with a decreasing series, where the correct concentrations are asymptotically approached from above rather than from below. The average of the two measurements (increasing and decreasing concentrations) provides a more accurate calculation, at the cost of double the total sample and double the measurement time. Following U.S. Pat. No. 6,651,009 by Trainoff et al., the '009 patent, one may define figures of merit, FOM, describing the magnitude of the $A_2$ and $A_3$ terms in the virial expansion of the light scattering equation, relative to the pure mass term; these are readily derived from Eq. (1) as $2A_2 Mc - 4A_2^2 M^2 c^2$ and $3A_3 Mc^2$, respectively. The assumption that the light scattering may be described by such a virial expansion implies convergence of the equation, i.e. the magnitudes of successively higher-order terms drop off fairly quickly; in other words 1>>FOM($A_2$)>>FOM($A_3$), and the smaller the figures of merit, the better the approximation. On the other hand, it is clear from considerations of signal-to-noise that the figures of merit must be of some finite value in order to obtain a reliable measurement. For a particular sample and instrument, the desirable upper and lower limits of the FOM for determining $A_2$ and $A_3$ are set by these considerations.

In U.S. Pat. No. 6,411,383 Wyatt describes a related method for measuring M, $\langle r_g^2 \rangle$, and $A_2$, using a single injection of unfractionated sample of finite volume, flowing through a MALS detector and a concentration detector. The sample injection is preceded and followed by sufficient pure solvent to bring the MALS and concentration signals back to baseline ($I_{solv}$) and is denoted a "peak" in the signal. Because of the finite nature of the sample, upon flowing through the system it is diluted and broadened so that different parts of the injection present different concentrations. Instead of applying Eq. (1) to multiple injections with a single value of $I(\theta)$ and c per injection, the inventor calculates the sums of $I(\theta)$, c and $c^2$ over the single peak, and determines $<r_g^2>$ and $A_2$ via Eq. (1) and a priori knowledge of M.

This method, utilizing a single flowing peak, is denoted herein as the "Wyatt peak" method. Since flow cell saturation is not required, a much smaller volume is required, typically in the range of 200-500 μL, where the maximum elution interval concentration corresponds to that which would be attained with the plateau method.

In passing from detector to detector, the sample peak is further broadened and reduced in height due to mixing and dilution. Hence the time-dependent concentration signal from the concentration detector does not precisely replicate the time-dependent concentration present in the light scattering detector. Since the light scattering signal is not a linear function of concentration, applying Eq. (1) to the sequential values of the light scattering and concentration leads to some degree of error in calculating the virial coefficients. The error in the Wyatt peak method increases both as the interdetector broadening increases, and as the deviation of the MALS signal from linear dependence on concentration increases, i.e. with larger FOM.

The '009 patent describes a correction factor intended to reduce this error, denoted herein the "Trainoff-Wyatt peak method". In this method, a series of peaks of different concentrations are injected into the detectors. Typical volumes of these injections are 100-200 μL. In the absence of interdetector broadening, it is possible to calculate the parameters of interest by summing $R(\theta)$, c and $c^2$ over each peak and fitting the sums to Eq. (1). Again, the broadening effect introduces errors into the calculation. The '009 patent shows that, in the case that the broadening causes only small changes to the widths of the peak, the error can be corrected by a simple multiplicative factor. This factor can be determined in several ways. The simplest is a calibration method in which the results of the injection method are compared to that of the plateau method for a reference standard. The correction factor determined thereby can be used for subsequent unknown samples. In the special case of Gaussian peaks, the correction factor can be inferred from the ratio of the peak widths. The limitation of this method is that it does not work well for large broadening, and it requires extra effort to determine the correction factor a priori.

Therefore, a method that employs flowing peaks for minimal sample quantities as in the '009 patent, but analyzes the peak data for M, $<r_g^2>$, $A_2$ and $A_3$ in a manner independent of inter-detector broadening effects, without restriction on the peak shape, would be advantageous.

Cross virial coefficients, measuring the interactions between different species of molecules A and B, are also quantities of fundamental importance in science and industry. The light scattering equation for a solution of two molecular species is presented in Eq. (3), to first order. As for the single-species case, the self- and cross-virial coefficients may be measured with a series of injections containing different concentrations, in this case of both species, fitting the light scattering and concentration values to the equation, analogous to the plateau method for $M_A$, $M_B$, $<r_g^2>_A$, $<r_g^2>_B$, $A_2^A$, $A_2^B$ and $A_2^{AB}$ where $A_2^A$ and $A_2^B$ may be considered "self-virial coefficients", and $A_2^{AB}$ the cross virial coefficient. A method for characterizing cross-virial coefficients using minimal sample quantities, akin to the Wyatt peak method for self-virial coefficients, would be advantageous.

$$\frac{R(c_A, c_B, \theta)}{K} = \left(\frac{dn}{dc_A}\right)^2 \{M_A c_A P_A(\theta) - 2A_2^A [M_A P_A(\theta) c_A]^2\} + \left(\frac{dn}{dc_B}\right)^2 \{M_B c_B P_B(\theta) - 2A_2^B [M_B P_B(\theta) c_B]^2\} - \left(\frac{dn}{dc_A} - \frac{dn}{dc_B}\right) 4A_2^{AB} M_A M_B P_A(\theta) P_B(\theta) c_A c_B. \quad (3)$$

Various types of on-line concentration detectors are known, including UV-visible absorbance, fluorescence, and differential refractive index, dRI, detectors. dRI detectors are particularly useful in combination with light scattering measurements, and are sufficiently versatile to measure a wide range of soluble macromolecules. One drawback of the dRI measurement is the necessity for completely dialyzing protein samples against the solvent, for the very reason that the dRI detector is sensitive to the salts and excipients, as well as dissolved gasses, that may be present in the protein sample but not in the pure buffer.

Dialysis is also important in the virial coefficient measurement because the virial coefficients vary with buffer conditions, and these must be well-defined for the measurement to be meaningful. In some instances, the effect of the buffer on the molecular interactions is determined by measuring virial coefficients under several different buffers, and aliquots of the same sample must be dialyzed against each buffer. However, dialysis can be a tedious and time-consuming process, and a means of combining the flowing peak measurement with in-line dialysis would be advantageous in automating these measurements.

SUMMARY OF THE INVENTION

It is an objective of this invention to provide a method to determine M, $<r_g^2>$, $A_2$ and $A_3$ directly from a sequence of injections of sample at different concentrations, with improved accuracy and reduced computational effort, using minimal quantities of samples, denoted herein as the "Online Virial Coefficient Method".

Another objective of the invention is the determination of cross-virial coefficients using minimal quantities of sample, based on the Online Virial Coefficient Method.

Yet another objective of the invention is to provide for increased automation by combining the dialysis process with the measurement, obviating the need for dialyzing samples with respect to different solvents prior to the injection.

BRIEF DESCRIPTION OF THE DRAWINGS

FIG. 5 shows (a) the 90° light scattering signal and concentration signal for the series of injections used to construct a Zimm plot of BSA in PBS with the Online Virial Coefficient Method; (b) a portion of the data plotted in (a), showing an individual peak.

DETAILED DESCRIPTION OF THE INVENTION

As in the '009 patent, the method begins with the preparation of a set of concentrations of the sample for injection through the flow cells of serially arranged MALS and concentration detectors. Two of the techniques that may be used to create the sample concentrations and deliver them to the detectors are the injection loop/injection valve method, and the dual-pump method, described below. Other embodiments of methods for creating and injecting peaks of different sample concentration will be evident to the knowledgeable practitioner.

Injection Valve Method:

In a first preferred embodiment, a stream of solvent flows continuously through the detectors by way of the injection valve, in the bypass position. While in the bypass position, sample is loaded into the sample loop. Then the valve is rotated to the inject position, inserting the sample loop into the flow path, and the sample is carried to the detectors. If an auto sampler is available, then a single stock solution of sample may be provided for subsequent automatic dilution to specified concentrations. There are two ways that that an autosampler may be used to prepare the concentrations. First, it can inject progressively smaller quantities of stock solution into the sample loop, under-filling it. Alternatively, the autosampler can be programmed to pre-dilute the sample before filling the sample loop, and then inject the diluted sample into the loop, typically with an equal volume of each concentration. The former method is preferred as it is simpler to implement. If no autosampler is present, then a series of samples at different concentrations may be prepared manually, or by any other method as may be known to those skilled in the art, for injection.

Dual-pump Method:

In a second preferred embodiment, the samples and solvent are mixed and flowed through the detectors by means of two pumps, one supplying sample stock and the other supplying solvent. The ratio of the flow rates of the pumps is adjusted to produce the desired dilution, such that the total flow rate achieves the desired value; the two streams are combined and pass through a mixer prior to reaching the detectors. The flow may be halted at any time before the sample reaches the detectors, e.g. in order to allow the diluted sample to homogenize, equilibrate, etc. After creating the desired volume of sample at the desired dilution, the pump providing sample stock solution is halted and the pump providing solvent is adjusted to match the desired total flow rate value, pushing the sample to the detectors.

In a third preferred embodiment, these two injection methods may be combined, wherein a dual-pump dilution system provides the diluted sample to the injection loop.

Upon reaching the MALS and concentration detectors, the signals measured by these detectors are acquired by a computer, stored and processed in order to calculate the molecular characteristics.

The calculation accounts for the fact that, while the sample is diluted in passage from one detector to the next, no sample is lost. Instead of the usual representation of the excess Rayleigh ratio as a series expansion in powers of concentration and angle (see Eq. (1)), the Zimm equation is inverted to provide a representation of concentration as a series expansion in powers of excess Rayleigh ratio and angle, with the same approximation order as the standard Zimm equation. The new equation is applied to the light-scattering data to obtain the concentration at each point in the peak passing through the MALS detector; then the concentration signals in both detectors are integrated to obtain the total sample mass in each peak. Since these masses are assumed equal, the integrated values from the two detectors may be equated. This procedure is repeated for the entire series of peaks at different concentrations, and the results fit to the equations to obtain the M, $<r_g^2>$, $A_2$ and $A_3$ parameters.

The calculation involves integrating the detector signals over the peaks, with the assumption of a constant flow rate through the detectors. Therefore it is important to maintain a constant flow rate while the sample is present in the detectors; however, prior to sample reaching the detectors and after return to baseline, the flow may be halted as necessary.

1.0 Single-species Characterization 1.1 Theoretical Description

The calculation relies on inverting the light scattering equation so as to represent $c=c(R^*,\theta)$. The inversion is most easily derived from a form of the standard Zimm equation (1):

$$\frac{c}{R*(c,\theta)} = \frac{1}{MP(\theta)} + 2A_2c + [3A_3Q(\theta) - 4A_2^2 MP(\theta)(1-P(\theta))]c^2. \quad (3)$$

This expansion may be readily inverted to yield:

$$c(R^*,\theta) = \frac{R^*}{M}\left(1 + P_1\sin^2\left(\frac{\theta}{2}\right) - P_2\sin^4\left(\frac{\theta}{2}\right)\right) + \frac{2A_2}{M}R^{*2}\left(1 + P_1\sin^2\left(\frac{\theta}{2}\right)\right) + \left(\frac{3A_3}{M^2} + \frac{4A_2^2}{M}\right)R^{*3}. \quad (4)$$

It is important to note that this describes the instantaneous concentration of the sample inside the light scattering detector. The concentration in the serially attached concentration detector will, in general, be slightly different due to the aforementioned effects of inter-detector broadening, even after correcting for the delay associated with the transit time between the two detectors. Although the instantaneous concentrations differ, conservation of mass guarantees that the total mass in each peak that passes through each detector is identical.

In the Online Virial Coefficient measurement, we equate the total mass of each peak as detected in the concentration and MALS detectors by integrating the concentration:

$$\sum_{conc.peak,i} c_i \Delta v_i = \sum_{L.S.peak,j} c_j \Delta v_j \quad (5)$$

where $c_i$ is the $i^{th}$ concentration measurement, acquired by the concentration detector, averaged over an eluted volume $\Delta v_i$, and $c_j$ is the $j^{th}$ concentration calculated from data acquired by the light scattering detector, averaged over an eluted volume $\Delta v_j$. For convenience we use the following notation, where $R(\theta)_j$ is the $j^{th}$ light scattering measurement of the excess Rayleigh ratio acquired by a photodetector at angle $\theta$, averaged over an eluted volume $\Delta v_j$:

$$C_m = \sum_{conc.peak,i} c_{mi} \Delta v_{mi};$$

$$R_{1,mk} = \sum_{L.S.peak,j} [R^*(\theta_k)_{mj}] \Delta v_{mj};$$

$$R_{2,mk} = \sum_{L.S.peak,j} [R^*(\theta_k)_{mj}]^2 \Delta v_{mj}; \text{ and}$$

$$R_{3,mk} = \sum_{L.S.peak,j} [R^*(\theta_k)_{mj}]^3 \Delta v_{mj}.$$

Equation (5) may be rewritten as:

$$C_m = \frac{1}{M} R_{1,mk} + \frac{P_1}{M} \sin^2\left(\frac{\theta}{2}\right) R_{1,mk} - \frac{P_2}{M} \sin^4\left(\frac{\theta}{2}\right) R_{1,mk} + \frac{2A_2}{M} R_{2,mk} + \frac{2A_2 P_1}{M} \sin^2\left(\frac{\theta}{2}\right) R_{2,mk} + \left(\frac{3A_3}{M} + \frac{4A_2^2}{M^2}\right) R_{3,mk}.$$ (6)

Fitting the data from a series of peaks of various concentrations to Eq. (6) determines the values of M, $<r_g^2>$, $A_2$ and $A_3$. In a similar fashion the virial expansion of R($\theta$,c) to any order may be inverted to obtain c($\theta$,R) in the comparable orders. The magnitude of the volume elements are determined from the elution time and flow rate. Since the MALS and concentration detectors are connected in series, the flow rate through both is identical and the volume elements may be replaced with time element $\Delta t_i$ and $\Delta t_j$. A key observation is that inter-detector band broadening affects the instantaneous concentration, $c_{mi}$, but not the integrated concentration, $C_m$. Therefore Eq. (6) is independent of inter-detector band broadening, which is a primary advantage of this method over earlier methods.

The method assumes that the total mass eluting through both detectors is equal; therefore the measurements and calculations must cover a range of eluting volume elements sufficient to include essentially all of the eluting sample.

1.2 Measurement Apparatus and Procedure

Figure 1:
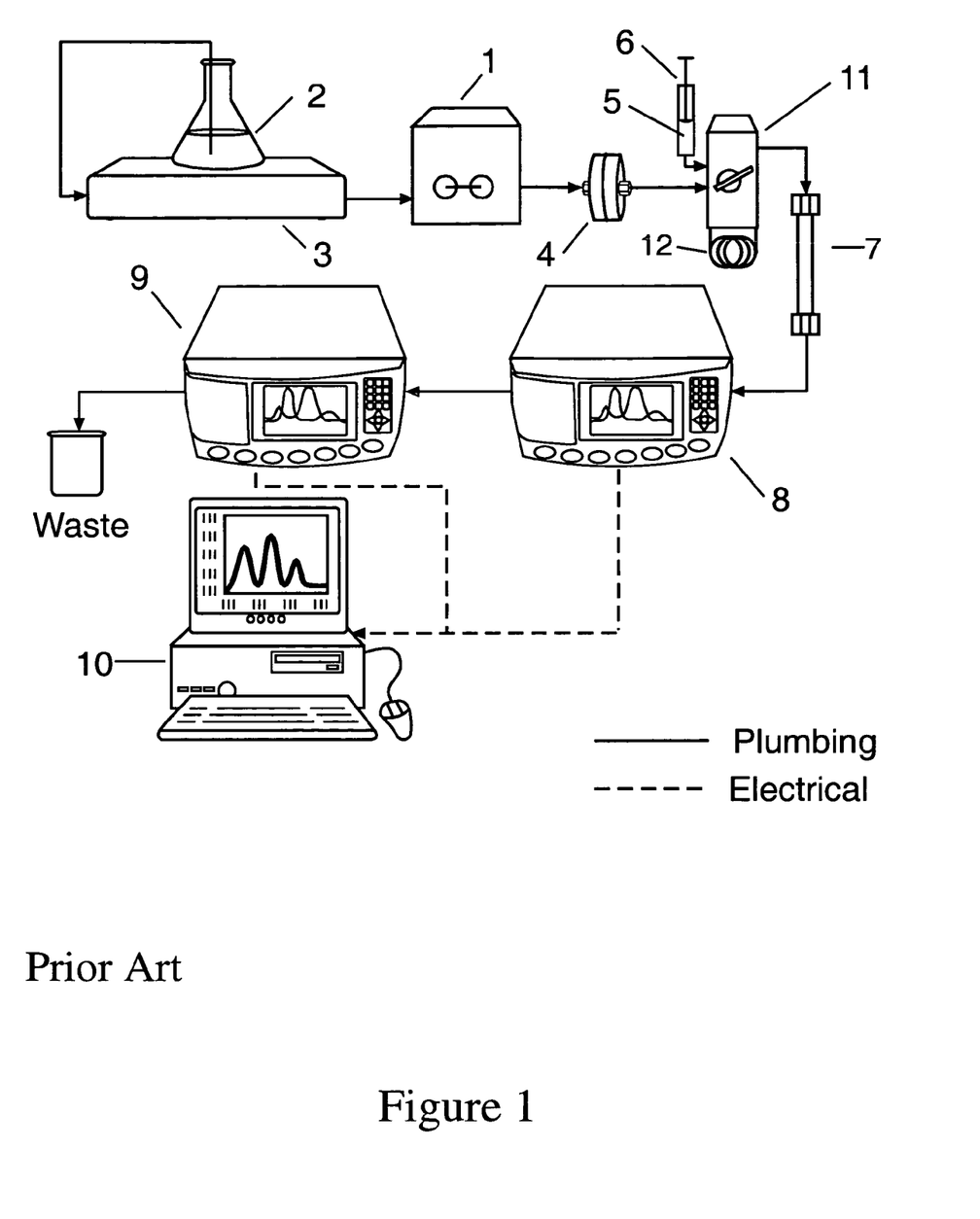
FIG. 1 is a diagram of the key elements of one preferred embodiment of the invention, the injection valve method.

A set of samples of initial concentrations $c_1, c_2, \ldots c_n$ are injected sequentially into a set of detectors—a MALS detector, comprising a photodetector at a plurality of angles $\theta_k$, and a concentration detector, such as shown in FIG. 1. One example of the MALS detector is the DAWN-HELEOS, from Wyatt Technology Corporation, Santa Barbara, Calif., and an example of a concentration detector is the Optilab rEX, also from Wyatt Technology Corporation. In a typical embodiment, the concentration series corresponds to $c_m = m\Delta c$, where m takes on integer values from 1 to n, and $\Delta c$ is a fixed concentration step. The actual peak concentrations will differ from the original values as the sample peaks dilute and broaden in the course of flowing through the system. The sample is caused to flow continuously through the detectors by means of a pump. As the sample passes through the detectors, data is acquired from the detectors, stored and analyzed by a computer performing the fitting procedure described previously.

In a first embodiment denoted the "injection valve method", depicted in FIG. 1, solvent is drawn by pumping means 1 from a solvent reservoir 2 through a degasser 3 and then pumped through filter means 4 to the injection valve 11 and on to the detectors 8 and 9. The degasser 3 is generally used to remove dissolved gasses from the solvent as such gasses might subsequently produce small bubbles in solution that could interfere with the desired measurements from the solution itself. Filter means 4 is generally incorporated as shown to remove residual particulate material from said solvent that could interfere with the desired measurements. One example of the pumping means is the model G1310 isocratic pump from Agilent Technologies, Inc., Santa Clara, Calif. An example of a degasser is the Systec Multi-Channel Vacuum Degasser, available from Upchurch Scientific, Oak Harbor, Wash. The solvent passes through the injection valve 11 set to bypass position so that the solvent does not flow through the sample loop 12. An example of an injection valve is the model 7725 analytical injector, also from Upchurch Scientific. Aliquots of the sample 5, whose weight average molar mass, mean square radius, and second and third virial coefficients are to be derived by the method of this invention, are transferred by injector means 6 into the sample loop 12. When the sample transfer is complete, the injection valve is switched to the inject position such that the solvent flows through the sample loop 12, carrying the sample to the detectors 8 and 9. The various concentrations can be prepared in advance and injected manually into the sample loop. Alternatively they may be prepared in advance and injected by means of an autosampler. In a preferred embodiment, a commercial autosampler, such as the 1329A, also from Agilent Technologies, Inc, is programmed to create the concentrations from a stock solution of sample by mixing different volumes of stock solution and solvent in a vial. In another preferred embodiment, the concentrations are created by programming an autosampler to inject different volumes of stock solution directly into the sample loop, where the sample loop is filled with solvent, and the injection volumes are smaller than the loop volume so that dilution occurs via mixing in the sample loop. Preferentially the samples would span an order of magnitude in concentration, or greater.

Figure 2:
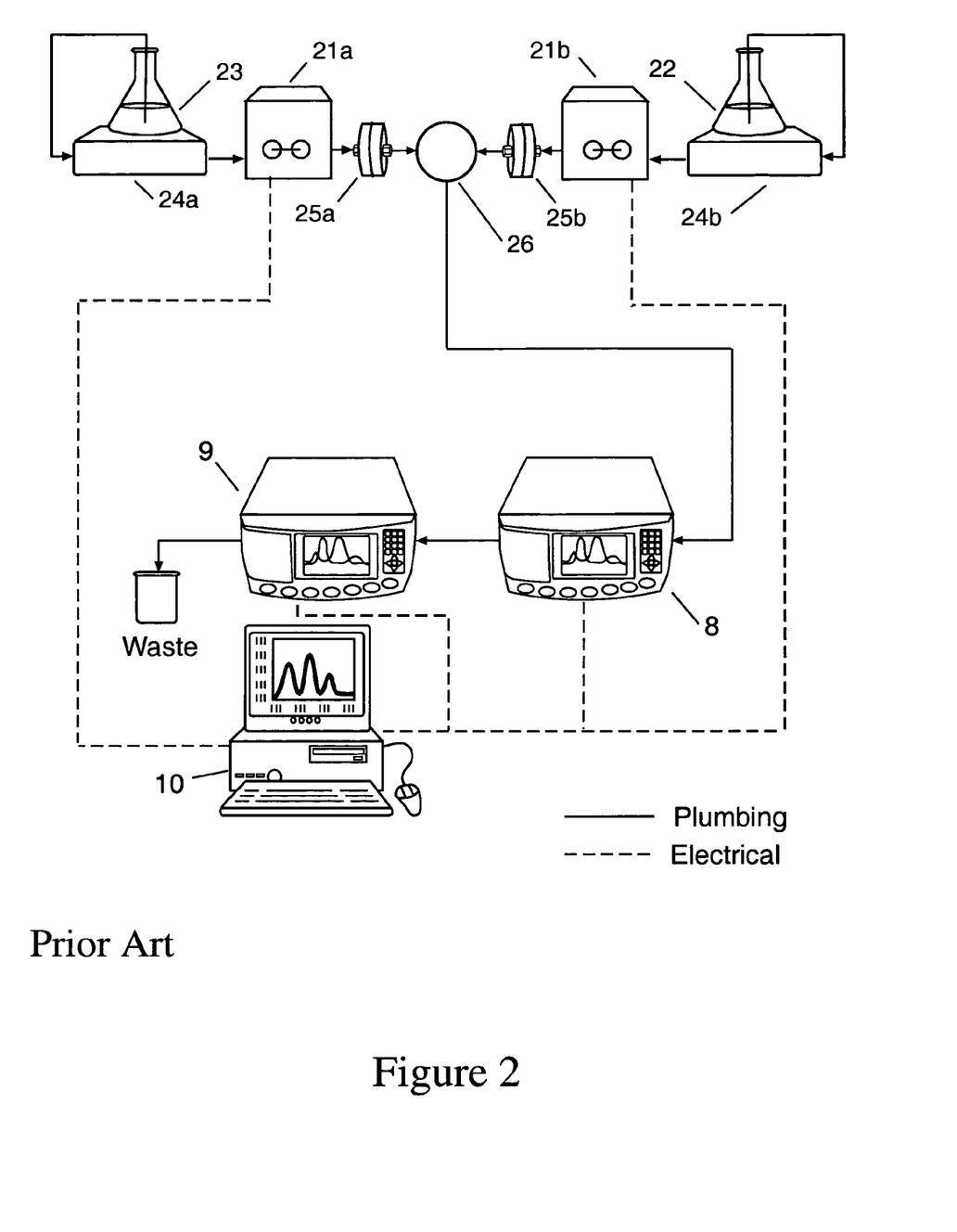
FIG. 2 is a diagram of the key elements of a second preferred embodiment of the invention, the dual-pump method.

In a second embodiment denoted the "dual-pump method", depicted in FIG. 2, two computer-controlled pumps 21a and 21b e.g. the Microlab 500 Dual-Syringe Diluter/Dispenser, Hamilton Corp., Reno, Nev., comprises two independently controllable syringe pumps, are used to draw sample from a sample reservoir 22 and solvent from a solvent reservoir 23. These are transferred through degasser chambers 24a and 24b and pumped through filters 25a and 25b. The flow rates of the two pumps are adjusted by means of the computer, and the streams combined and pumped through a mixing chamber, e.g. the Hypershear in-line static mixer, available from Analytical Scientific Instruments, El Sobrante, Calif., in order to produce a continuous stream of sample at the desired concentration. The mixed sample may be temporarily stored in a holding volume 26 which includes the mixing chamber, tubing, desalting column, and any additional volume as may be required. After the desired volume of mixed sample has been injected into the holding volume, the flow of sample stock solution is stopped, and solvent is pumped by pump 21a so as to cause the sample to flow from the holding volume through the detectors at the desired flow rate. The preferred range of dilutions is as in the previous embodiment.

As would be evident to those skilled in the art, a third embodiment would create sequential sample concentrations with a pair of pumps as per the dual pump method, injecting the mixed sample into a sample loop, and the sample would be pushed on to the detectors by an additional pumping means upon switching the injection valve, as per the injection valve method.

In the event that the sample requires prior dialysis, a desalting column 7, e.g., the HiTrap desalting column, available from Amersham BioSciences, Uppsala, Swede, may be placed before the MALS detector 8.

Each successive sample 5 passes through the MALS detector 8, whereby the values of the excess Rayleigh ratio at each angle, $R_j(\theta_k)$, are measured at successive elution volumes $\Delta v_j$; and through a concentration detector 9, shown as a differential refractive index (dRI) detector, whereby the sample concentration $c_i$ is measured at each volume interval $\Delta v_i$. The resultant light scattering and concentration signals are then stored and processed by computer means 10 to calculate, for each injected aliquot m, the values $C_m$, $R_{1,mk}$, $R_{2,mk}$, and $R_{3,mk}$. Computer means 10 also computes the molecular characteristics including M, $\langle r_g^2 \rangle$, $A_2$ and $A_3$ by fitting the calculated results to Eq. (6). Various fitting procedures may be implemented to extract the molecular characteristics. In the event that the angular dependence is negligible, or the $A_3$ term is negligible, a linear least-squares fit is one preferred embodiment. In another preferred embodiment, the fitting procedure consists of a non-linear least squares fit employing the Levenberg-Marquardt algorithm. As is known to those skilled in the art, a lower-order fit may be performed, dropping, e.g. the $A_3$ term, if the quality of the data or the FOM do not merit keeping all the higher-order terms.

Although the sample concentration detector 9 may be a dRI detector, an ultraviolet or visible light absorption detector may be substituted. An evaporative light scattering detector also may be used to monitor each eluting sample's concentration, though such a device may need special calibration, as its response is generally non-linear. Other online detectors are known to those skilled in the art.

As will be evident to those skilled in the art, the fitting of the measured data to the form of Eq. (6), whether by linear least squares method, the Levenberg-Marquardt method, or other algorithms, may include statistical weighting whereby the data used to perform these fits is weighted by their measured standard deviations.

1.3 An Example of the Method

To demonstrate the utility of the method, we present the measurement of the molecular parameters of bovine serum albumin, BSA, dissolved in aqueous phosphate buffer solution, PBS. The sample, from Sigma-Aldrich Corporation, has a monomer molecular weight of 66,400 (the actual weight-averaged molar mass is slightly higher due to the presence of low concentrations of dimers and trimers) and a mean-square radius below the limit measurable by scattering of visible light (using the static light scattering technique).

Figure 3:
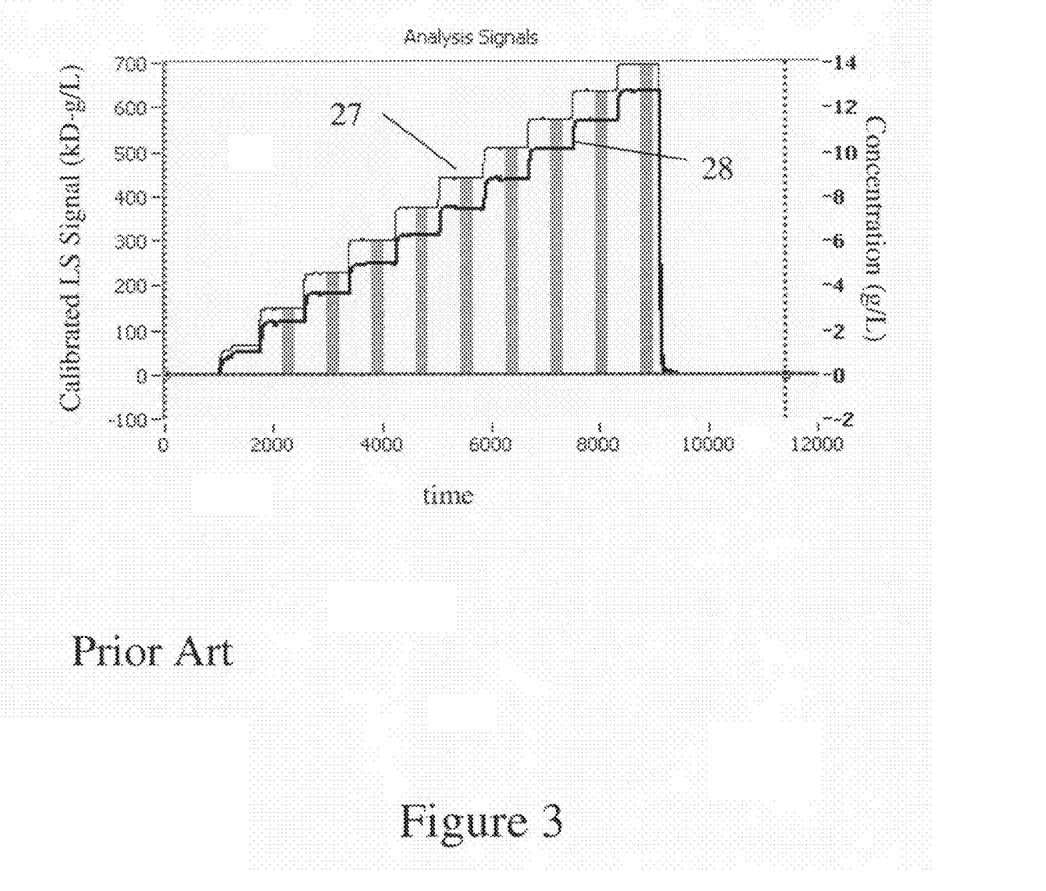
FIG. 3 shows the 90° light scattering signal and concentration signal for the series of injections used to construct a Zimm plot of bovine albumin serum (BSA) in phosphate buffer solution (PBS).
Figure 4:
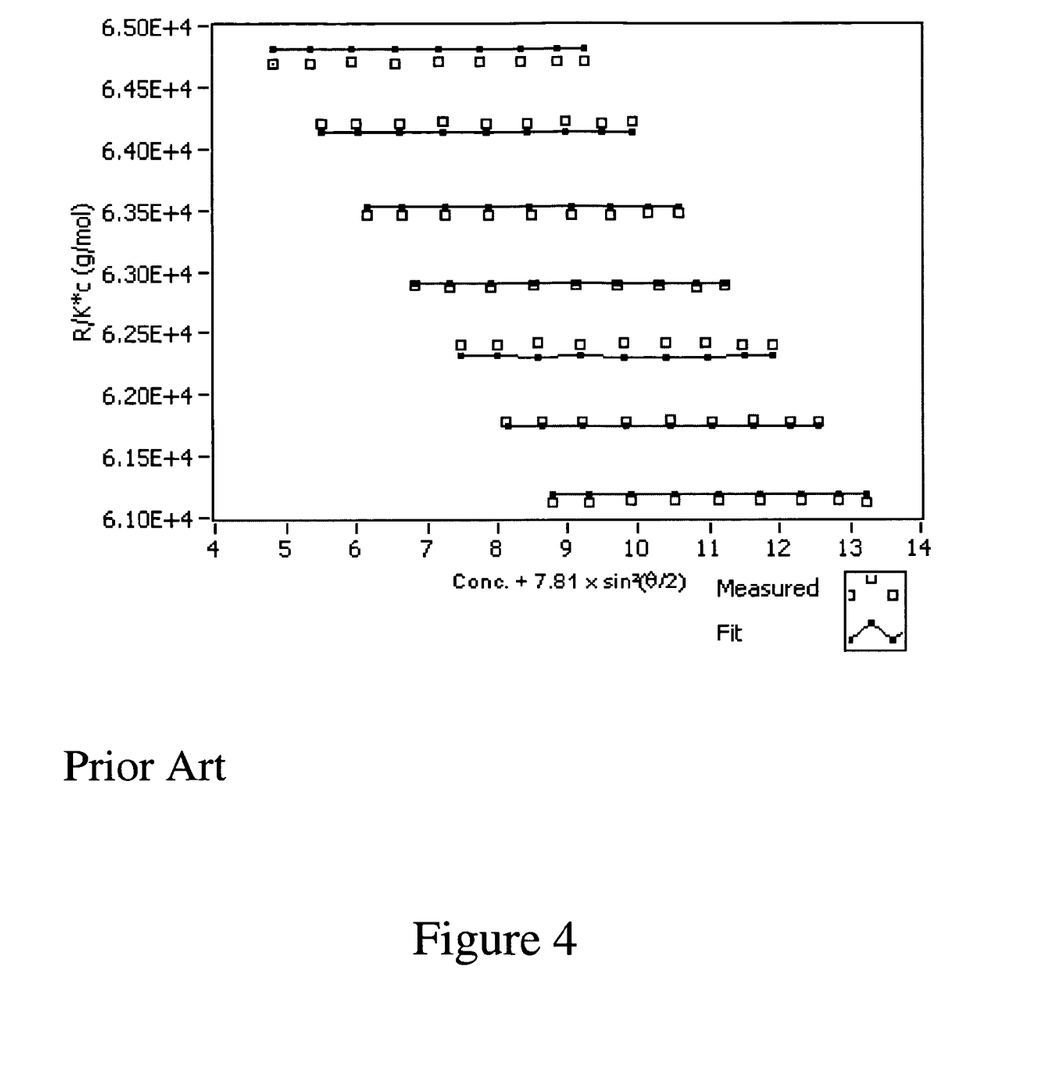
FIG. 4 is a traditional Zimm plot of BSA dissolved in PBS, based on the plateau data of FIG. 3 and the standard analysis via the plateau method applied to the data of FIG. 4.

The sample was characterized using two methods. The first method is the plateau method. A sample stock solution was prepared at a concentration of 10 g/L. The stock solution and solvent were drawn through degassing chambers, filtered and mixed to the desired concentration series in a static mixer, at fixed concentration intervals, by means of a triple syringe pump diluter/dispenser. A sufficiently large volume of sample—2 mL—was injected into serially connected MALS and concentration detectors, so as to fill the flow cells and bring each signal to a plateau. The raw signal from the 90° light scattering detector 27 as well as that from the concentration detector 28 is shown in FIG. 3. The plateaus are clearly visible and a small range of data on the plateau of each peak were averaged and used to generate the Zimm plot shown in FIG. 4. The measured quantities are M=67,760±0.05 kD and $A_2$=1.33±0.01×10$^{-4}$ mol·mL/g$^2$. The data are of high quality, but relatively large quantities of sample (~2 mL per aliquot) are required.

Figure 5A:
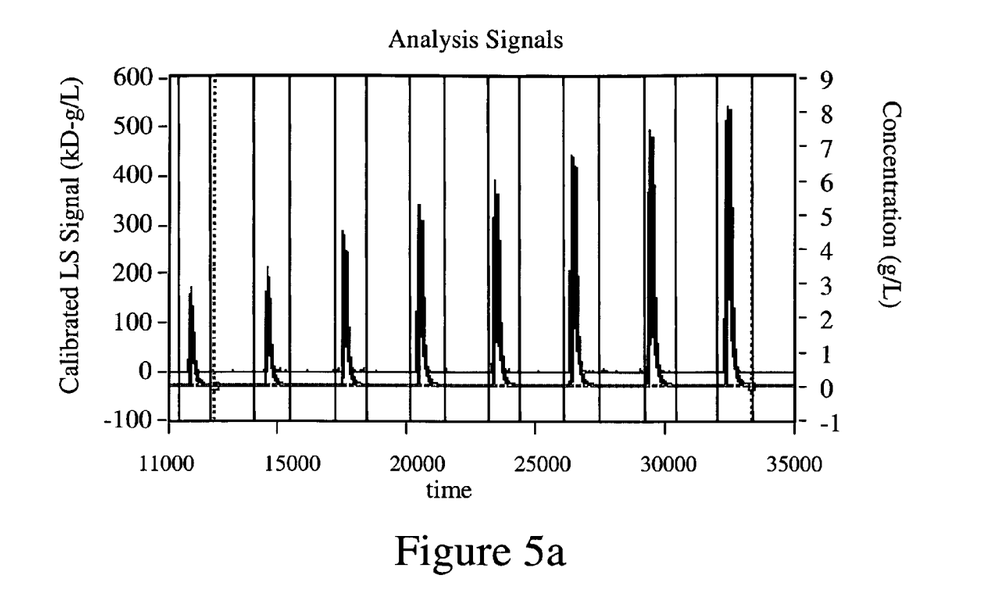
Figure 5B:
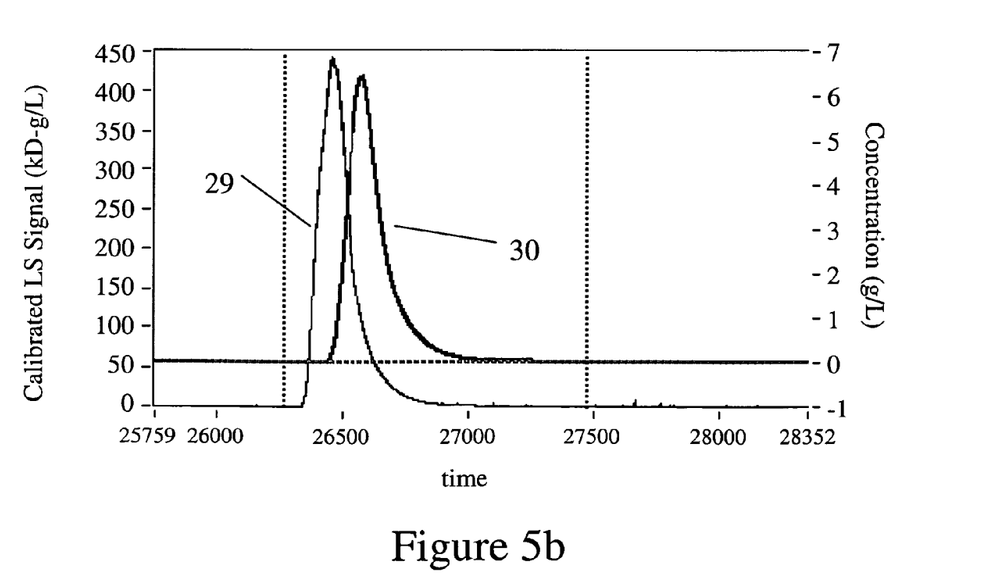
Figure 6:
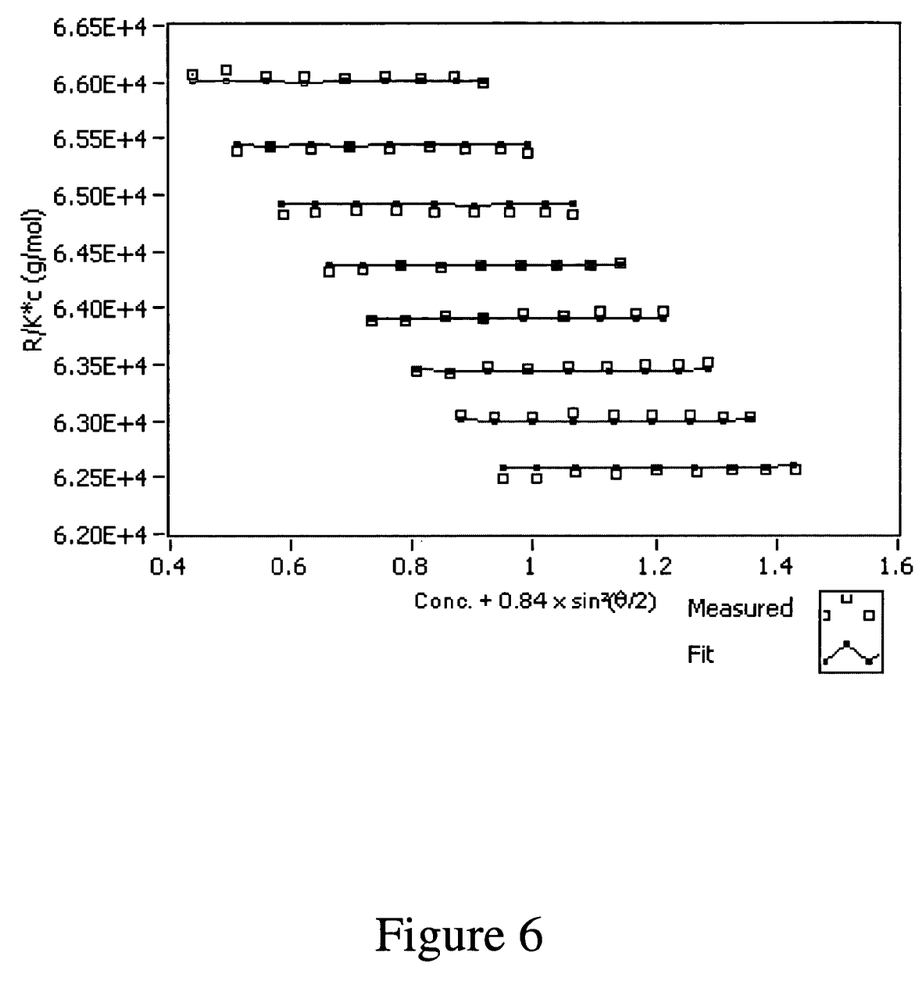
FIG. 6 is a Zimm plot using the Online Virial Coefficient analysis, applied to the data of FIG. 5.

The second method is the subject of this invention. The same sample concentrations were injected via the dual pump method, using only 200 µl per injection so that the flow cell was not completely filled and plateaus were not achieved. The data is shown in FIG. 5. It shows the 90° light scattering signal 29 overlaid with the dRI detector signal 30. Both have been baseline subtracted. From each injection, $c_m$, $R_{1,mk}$, $R_{2,mk}$, and $R_{3,mk}$ are computed. The resulting fit to Eq. (6), using the linear least squares fit method, is shown in FIG. 6. The results obtained were M=66,700±0.03 kD and $A_2$=1.17±0.01×10$^{-4}$ mol·mL/g$^2$. These values agree well with those obtained via the plateau method.

2.0 Dual-species Characterization:

2.1 Theoretical Description:

The light scattering equation, up to second order in concentration, for two non-associating macromolecular species present in a solvent is given by Eq. 7:

$$\frac{R(c_A, c_B, \theta)}{K} = \left(\frac{dn}{dc_A}\right)^2 \{M_A c_A P_A(\theta) - 2A_2^2[M_A P_A(\theta)c_A]^2\} + \left(\frac{dn}{dc_B}\right)^2 \{M_B c_B P_B(\theta) - 2A_2^B[M_B P_B(\theta)c_B]^2\} - \left(\frac{dn}{dc_A}\frac{dn}{dc_B}\right) 4A_2^{AB} M_A M_B P_A(\theta) P_B(\theta) c_A c_B. \quad (7)$$

Here $dn/dc_A$ and $dn/dc_B$ are the differential refractive increment of species A and B, $M_A$ and $M_B$ the weight-averaged molar mass of species A and B, $c_A$ and $c_B$ the concentrations of species A and B, $P_A(\theta)$ and $P_B(\theta)$ the angular distributions due to species A and B assuming $\langle r_g^2 \rangle_A$ and $\langle r_g^2 \rangle_B$, $A_2^A$ and $A_2^B$ the self-virial coefficients of species A and B, and $A_2^{AB}$ the cross-virial coefficients of species A and B. The values of $M_A$, $M_B$, $\langle r_g^2 \rangle_A$, $\langle r_g^2 \rangle_B$, $A_2^A$ and $A_2^B$ may be determined by the single-species method described above.

The remaining parameter, $A_2^{AB}$, may now be determined in a measurement combining the two species. The measurement will consist of a sequence of samples with differing concentrations of species A and species B, and will consist of small, continuously flowing aliquots, in order to enjoy the advantages of the online virial coefficient method.

In order to invert the equation as described for a single scattering species, and additional relationship is required. For that relationship we can safely assume that throughout the injection of each aliquot m, the ratio $f_m$ of $c_B$ to $c_A$ is constant and known (since it is determined by the apparatus), even though the magnitude of these concentrations varies because mixing affects both species equally:

$$c_{B,m} = f_m c_{A,m}. \quad (8)$$

Equations (7) and (8) may be combined to yield an expression for $R=R(c_A,\theta)$ which may be inverted to express $c_A = c_A(R,\theta)$:

$$c_A(R^*, \theta) = \frac{R}{KX^{AB}} + \frac{\left(\frac{dn}{dc_A}\right)^2 M_A P_1^A + \left(\frac{dn}{dc_B}\right)^2 f M_B P_1^B}{K(X^{AB})^2} R\sin^2\left(\frac{\theta}{2}\right) + \frac{\left(\frac{dn}{dc_A}\right)^2 2A_2^A M_A^2 + \left(\frac{dn}{dc_B}\right)^2 2A_2^B f^2 M_B^2 + \frac{dn}{dc_A}\frac{dn}{dc_B} 4A_2^{AB} f M_A M_B}{K(X^{AB})^3} R^2, \quad (9)$$

where terms higher than second order in R or $\sin^2(\theta/2)$ have been ignored, and the following variables defined:

$$X^{AB} = \left(\frac{dn}{dc_A}\right)^2 M_A + \left(\frac{dn}{dc_B}\right)^2 fM_B;$$

$$P_1^A = [(4k^2/3) < r_g^2 >_A; \text{ and } P_1^B = [4k^2/3] < r_g^2 >_B.$$

The total mass of A in each injection m as calculated from the concentration signals may be equated, by virtue of mass conservation, with that obtained from the light scattering by virtue of Eq. (9) and (5):

$$\sum_i c_{A,mi}\Delta v_i = \sum_i c_{mi}\Delta v_i/(1+f_m) = C_m, \quad (10)$$

where $c_{mi} = c_{A,mi} + c_{B,mi}$, $$C_m = \frac{R_{1,mk}}{K(X^{AB})} + \frac{\left(\frac{dn}{dc_A}\right)^2 M_A P_1^A + \left(\frac{dn}{dc_B}\right)^2 f^m M_B P_1^B}{K(X^{AB})^2} \sin^2\left(\frac{\theta}{2}\right) R_{1,mk} + \quad (11)$$

$$\frac{\left(\frac{dn}{dc_A}\right)^2 2A_2^A M_A^2 + \left(\frac{dn}{dc_B}\right)^2 2A_2^B (f^m)^2 M_B^2 + }{}$$

$$\frac{\frac{dn}{dc_A}\frac{dn}{dc_B} 4A_2^{AB} f^m M_A M_B}{K(X^{AB})^3} R_{2,mk}.$$

Carrying out the measurement over a range of values of $c_A$ and $c_B$ and fitting the results to equations (10) and (11) will determine the cross-virial coefficient $A_2^{AB}$.

As will be obvious to one skilled in the art, the order of the virial expansion may be increased to include higher-order parameters, e.g. $A_3^A$ or $A_3^B$.

2.2 Measurement Apparatus and Procedure

The measurement proceeds as for a single-species measurement, except that the samples include: 1) a series of concentrations of species A alone; 2) a series of concentrations of species B alone; and 3) a series of samples comprising both A and B in different concentrations. Parts (1) and (2) are necessary in order to obtain an unambiguous measurement of $A_2^{AB}$.

In one preferred embodiment, the ratio of $c_A$ to $c_B$ is fixed throughout all the two-component aliquots such that the ratio of the molarities of the two samples is 1:1.

In another preferred embodiment, the proportion of A and B is varied throughout the two-component aliquots across the entire range of ratios, from pure A, to pure B, at a fixed total concentration.

The apparatus is similar to those of the single-species measurement, except that in a preferred embodiment, the dual pump is replaced by a triple pump, each pump controllable by means of computer to pump species A, species B, and solvent. Such a triple pump is the Calypso system, available from Wyatt Technology Corporation, Santa Barbara, Calif.

As will be evident to those skilled in the arts of light scattering, there are many obvious variations of the methods we have invented and described that do not depart from the fundamental elements that we have listed for their practice; all such variations are but obvious implementations of the invention described hereinbefore and are included by reference to our claims, which follow.

What is claimed is:

1. A method to determine the average molecular properties of a solution of molecules in a solvent, said average molecular properties being the weight average molar mass M, the mean square radius $<r_g^2>$, the $2^{nd}$ virial coefficient $A_2$, and the $3^{rd}$ virial coefficient $A_3$, comprising the steps of A. providing a reservoir of said solvent;

B. providing a reservoir of said solution;

C. preparing from said reservoirs a series of n dilutions $D_m(m=1,n)$ of said solution, using a dilution means, by said solvent;

D. providing sampling means by which said dilutions $D_m(m=1,n)$ are sequentially injected and made to flow through serially a. a light scattering detection means that collects light scattered at a plurality of q angles $\theta_k(k=1,q)$ at each incremental injection volume $\Delta v_i$ of said dilution $D_m(m=1,n)$;

b. a concentration detection means that measures the corresponding molecular concentrations $c_{mi}(m=1,n)$ at each incremental injection volume $\Delta v_i$ of said dilution $D_m(m=1,n)$;

E. generating from the measured scattered light intensities and the corresponding concentration $c_{mi}$ at each flow volumetric incremental interval $\Delta v_i$ the associated excess Rayleigh ratios $R^*(\theta_k, c_{mi})$;

F. calculating the n concentration sums $$C_m = \sum_i c_{mi}\Delta v_i$$

corresponding to each said dilution $D_m$, where m=1 to n, from said collected molecular concentration values, $c_{mi}$, over the entire elution of each said dilution m;

G. calculating the 3qn excess Rayleigh ratios sums, $$R_{1,mi} = \sum_i [R^*(\theta_k, c_{mi})]\Delta v_i, (k=1, q;$$

$$m=1, n), R_{2,mk} = \sum_i [R*(\theta_k, c_{mi})]^2\Delta v_i,$$

$$R_{3,mk} = \sum_i [R^*(\theta_k, c_{mi})]^3\Delta v_i$$

corresponding to said n dilutions, from said generated excess Rayleigh ratios $R^*(\theta_k, c_{mi})$;

H. extracting said average molecular properties of said solution of molecules from said 3qn excess Rayleigh ratios sums by fitting the collected concentration values and generated excess Rayleigh ratio values with an appropriate equation relating said concentration sums and said excess Rayleigh ratio sums with variables representative of said average molecular properties of said solution of molecules as the parameters of the fit.

2. The method of claim 1 where said appropriate equation is $$C_{mk} = \frac{1}{M}R_{1,mk} + \frac{P_1}{M}\sin^2\left(\frac{\theta}{2}\right)R_{1,mk} - \frac{P_2}{M}\sin^4\left(\frac{\theta}{2}\right)R_{1,mk} + \frac{2A_2}{M}R_{2,mk} +$$
$$\frac{2A_2 P_1}{M}\sin^2\left(\frac{\theta}{2}\right)R_{2,mk} + \left(\frac{3A_3}{M} + \frac{4A_2^2}{M^2}\right)R_{3,mk} \text{ where } P_1 =$$
$$\frac{4\kappa^2}{3}\langle r_g^2\rangle, P_2 = \frac{2\kappa^4}{45}\left(10\langle r_g^2\rangle^2 - 3\langle r_g^4\rangle\right),$$

$$\kappa = \frac{2\pi n_0}{\lambda_0},$$

$n_0$ is the refractive index of the solvent and $\lambda_0$ is the incident vacuum wavelength of said light scattering detector, and the weight average molar mass M, the mean square radius $\langle r_g^2\rangle$, the $2^{nd}$ virial coefficient $A_2$ and the $3^{rd}$ virial coefficient $A_3$ are the parameters of the fit.

3. The method of claim 1 where said appropriate equation is $$C_m = \frac{1}{M}R_{1,mk} + \frac{P_1}{M}\sin^2\left(\frac{\theta_k}{2}\right)R_{1,mk} -$$
$$\frac{P_2}{M}\sin^4\left(\frac{\theta_k}{2}\right)R_{1,mk} + \frac{2A_2}{M}R_{2,mk} + \frac{2A_2 P_1}{M}\sin^2\left(\frac{\theta_k}{2}\right)R_{2,mk}, \text{ where}$$
$$P_1 = \frac{4\kappa^2}{3}\langle r_g^2\rangle, P_2 = \frac{2\kappa^4}{45}\left(10\langle r_g^2\rangle^2 - 3\langle r_g^4\rangle\right), \kappa = \frac{2\pi n_0}{\lambda_0},$$

$n_0$ is the refractive index of the solvent and $\lambda_0$ is the incident vacuum wavelength of said light scattering detector, and the weight average molar mass M, the mean square radius $\langle r_g^2\rangle$, the $2^{nd}$ virial coefficient $A_2$, and $P_2$ are the parameters of the fit.

4. The method of claim 1 where said appropriate equation is $$C_m = \frac{1}{M}R_{1,mk} + \frac{2A_2}{M}R_{2,mk} + \frac{2A_2 P_1}{M}\sin^2\left(\frac{\theta_k}{2}\right)R_{2,mk},$$

where $$P_1 = \frac{4\kappa^2}{3}\langle r_g^2\rangle, \kappa = \frac{2\pi n_0}{\lambda_0},$$

$n_0$ is the refractive index of the solvent and $\lambda_0$ is the incident vacuum wavelength of said light scattering detector, and the weight average molar mass M, the mean square radius $\langle r_g^2\rangle$, and the $2_{nd}$ virial coefficient $A_2$ are the parameters of the fit.

5. The method of claim 1 where said appropriate equation is $$C_m = \frac{1}{M}R_{1,mk} + \frac{2A_2}{M}R_{2,mk} + \left(\frac{3A_3}{M} + \frac{4A_2^2}{M^2}\right)R_{3,mk},$$

and the weight average molar mass M, the $2_{nd}$ virial coefficient $A_2$, and the $3^{rd}$ virial coefficient $A_3$ are the parameters of the fit.

6. The method of claim 1 where said appropriate equation is $$C_m = \frac{1}{M}R_{1,mk} + \frac{2A_2}{M}R_{2,mk},$$

and the weight average molar mass M and the $2_{nd}$ virial coefficient $A_2$ are the parameters of the fit.

7. The method of claim 1 where said fitting is performed by computer means.

8. The method of claim 1 where said fitting is a linear least squares fit.

9. The method of claim 1 where said fitting is a Levenberg-Marquardt non-linear least squares fit.

10. The method of claim 1 where said concentration detection means comprises a differential refractive index, dRI, detector.

11. The method of claim 1 where said concentration detection means comprises an ultraviolet, UV, absorption detector.

12. The method of claim 1 where said dilution means comprises an autosampler.

13. The method of claim 12 where said autosampler is operated so as to inject different volumes of a solution at fixed concentration into a sample loop of fixed volume filled with solvent, thereby producing dilution via mixing in the sample loop.

14. The method of claim 12 where said autosampler is operated so as to inject aliquots consisting of solutions originating from vials of sample prepared at different concentrations.

15. The method of claim 1 where said dilution means comprises a dual pump system.

16. The method of claim 15 where said sampling means comprises that pump of said dual pump system which provides the solvent.

17. The method of claim 16 wherein said dilution $D_m$ is deposited into a holding volume prior to reaching said light scattering and concentration detection means.

18. The method of claim 15 where said dilution $D_m$ is mixed by means of a static mixer.

19. The method of claim 1 where said sampling means further comprises a pump causing solvent to first flow through a sample loop into which said dilution $D_m$ has been inserted upstream from said light scattering and concentration detection means.

20. The method of claim 15 where one pump of said dual pump system provides said solution and the other pump of said dual pump system provides said solvent, whereby the two pumps are operated at a flow rate ratio determined to provide the desired dilution.

21. The method of claim 1 further comprising the step of having a desalting column placed in the flow path prior to said concentration and light scattering detection means, said desalting column providing means by which the sample is dialyzed against the solvent.

22. A method to determine the cross virial coefficient $A_2^{AB}$ of a solution of molecules in a solvent, said solution comprising two distinct macromolecular species A and B of known molar mass, $M_A$, $M_B$, known 2nd self-virial coefficient $A_2^A$ and $A_2^B$, and known mean square radius $\langle r_g^2\rangle_A$ and $\langle r_g^2\rangle_B$, comprising the steps of A. providing a reservoir of a solution said macromolecular species A;
B. providing a reservoir of a solution said macromolecular species B;
C. providing a reservoir of said solvent;
D. preparing from said reservoirs a series of n samples $S_m(m=1,n)$ of different compositions of said macromolecular species with said solvent using a sample mixing means, said samples spanning a range of concentrations and/or concentration ratios;
E. providing sampling means by which said samples $S_m(m=1,n)$ are sequentially injected and made to flow through serially
   a. a light scattering detection means that collects light scattered at a plurality of q angles $\theta_k(k=1,q)$ at each incremental injection volume $\Delta v_i$ of said sample $S_m(m=1,n)$;
   b. a concentration detection means that measures the corresponding molecular concentrations $c_{mi}(m=1,n)$ at each incremental injection volume $\Delta v_i$ of said sample $S_m(m=1,n)$;
F. generating from the measured scattered light intensities and the corresponding concentration $c_{mi}$ at each flow volumetric incremental interval $\Delta v_i$ the associated excess Rayleigh ratios $R^*(\theta_k, c_{mi})$;
G. calculating the n concentration sums $$C_m = \frac{1}{1+f_m} \sum_i c_{mi} \Delta v_i$$

corresponding to said samples $S_m$, where m=1 to n, from said collected concentration data values, $c_{mi}$, over the entire elution of each aliquot $S_m$, and $f_n$ is the known ratio of concentrations of A and B present in aliquot $S_m$;
H. calculating the 2qn excess Rayleigh ratios sums, $$R_{1,mk} = \sum_i [R^*(\theta_k, c_{mi})] \Delta v_i$$

and $$R_{2,mk} = \sum_i [R^*(\theta_k, c_{mi})]^2 \Delta v_i, \ (k=1,q; m=1,n),$$

corresponding to said n samples, from said generated excess Rayleigh ratios $R^*(\theta_k, c_{mi})$;
I. extracting said cross virial coefficient $A_2^{AB}$ of said samples by fitting the collected concentration values and generated excess Rayleigh ratio values with an appropriate equation relating said concentration sums and said excess Rayleigh ratio sums, with said cross virial coefficient as the parameter of the fit.

23. The method of claim 22 wherein said appropriate equation is $$C_m = \frac{R_{1,mk}}{KX^{AB,m}} +$$

-continued $$\frac{4\kappa^2}{3} \frac{\left[\left(\frac{dn}{dc_A}\right)^2 M_A \langle (r_g^A)^2 \rangle + \left(\frac{dn}{dc_B}\right)^2 f_m M_B \langle (r_g^B)^2 \rangle\right] \sin^2\left(\frac{\theta_k}{2}\right)}{(X^{AB,m})^2} \frac{R_{1,mk}}{K} +$$

$$\frac{\left(\frac{dn}{dc_A}\right)^2 2A_2^A M_A^2 + \left(\frac{dn}{dc_B}\right)^2 2A_2^B (f_m M_B)^2 \frac{dn}{dc_A} \frac{dn}{dc_B} 4A_2^{AB} f_m M_A M_B}{(X^{AB,m})^3}$$

$$\frac{R_{2,mk}}{K}, \text{where}$$

$$K = \frac{\kappa^2}{N_A \lambda_0^2}, \kappa = \frac{2\pi n_0}{\lambda_0},$$

$n_0$ is the refractive index of the solvent, $\lambda_0$ is the incident vacuum wavelength of said light scattering detector, $N_A$ is Avogadro's number, $$X^{AB,m} = \left[\left(\frac{dn}{dc_A}\right)^2 M_A + \left(\frac{dn}{dc_B}\right)^2 f_m M_B\right], \text{ and } \frac{dn}{dc_A}, \frac{dn}{dc_B}$$

are the refractive increments of A and B, respectively.

24. The method of claim 22 where said fitting is performed by computer means.

25. The method of claim 22 where said fitting is a linear least squares fit.

26. The method of claim 22 where said fitting is a Levenberg-Marquardt non-linear least squares fit.

27. The method of claim 22 where said concentration detection means comprises a differential refractive index, dRI, detector.

28. The method of claim 22 where said concentration detection means comprises an ultraviolet, UV, absorption detector.

29. The method of claim 22 where the average solution properties, molar mass, $M_A$, $M_B$; 2nd self-virial coefficient $A_2^A$ and $A_2^B$; and mean square radius $\langle r_g^2 \rangle_A$ and $\langle r_g^2 \rangle_B$; of said two distinct macromolecular species A and B have been determined by means of the method of claim 1.

30. The method of claim 22 where said sampling means comprises an autosampler.

31. The method of claim 30 wherein said autosampler is operated so as to inject aliquots consisting of solutions originating from vials of sample prepared at different concentrations and/or concentration ratios.

32. The method of claim 22 where said sample mixing means is a triple pump system.

33. The method of claim 32 where said sampling means comprises that pump of said triple pump system which provides the solvent.

34. The method of claim 32 wherein said sample is deposited into a holding volume prior to reaching said light scattering and concentration detection means.

35. The method of claim 22 where said sample mixing means comprises a static mixer.

36. The method of claim 22 where said sampling means comprises a pump causing solvent to flow through a sample loop into which said sample $S_m$ has been inserted upstream from said light scattering and concentration detection means.

37. The method of claim 33 wherein two pumps of said triple pump system provide said solutions of each of the said distinct macromolecular species, and the third pump provides said solvent, whereby the three pumps are operated at a flow rate ratio designed to provide the desired concentrations and concentration ratios.

38. The method of claim 22 further comprising the step of having a desalting column placed in the flow path upstream from said light scattering and concentration detection means, said desalting column providing means by which said solution is dialyzed against said solvent.

39. The method of claim 22 where said concentration ratio between the two said macromolecular species is fixed across all said samples made to include both said macromolecular species.

40. The method of claim 22 where the concentration ratio between the two said macromolecular species is varied across all said samples made to include both said macromolecular species.

* * * * *